(12) United States Patent
Buck

(10) Patent No.: US 9,603,736 B1
(45) Date of Patent: Mar. 28, 2017

(54) ENHANCED FOREFOOT PROTECTION FOR ORTHOPEDIC REHABILITATION DEVICES

(71) Applicant: David C. Buck, Elkhorn, NE (US)

(72) Inventor: David C. Buck, Elkhorn, NE (US)

( * ) Notice: Subject to any disclaimer, the term of this patent is extended or adjusted under 35 U.S.C. 154(b) by 322 days.

(21) Appl. No.: 14/502,233

(22) Filed: Sep. 30, 2014

Related U.S. Application Data

(60) Provisional application No. 61/885,708, filed on Oct. 2, 2013.

(51) Int. Cl.
 *A61F 5/01* (2006.01)

(52) U.S. Cl.
 CPC ...... *A61F 5/0195* (2013.01); *A61F 2250/006* (2013.01)

(58) Field of Classification Search
 CPC .... A61F 5/0102; A61F 5/0113; A61F 13/066; A61F 5/0585; A61F 5/0111; A61F 5/0127; A43B 7/20
 See application file for complete search history.

(56) References Cited

U.S. PATENT DOCUMENTS

| | | | |
|---|---|---|---|
| 2,354,338 A | 7/1944 | Stritter | |
| 2,756,519 A | 7/1956 | Hill | |
| 3,444,572 A | 5/1969 | Broughton | |
| 3,798,804 A | 3/1974 | Funck | |
| 6,604,303 B2 | 8/2003 | Covatch | |
| 2007/0255191 A1* | 11/2007 | Cozzo | A43B 5/14 602/23 |
| 2010/0174219 A1* | 7/2010 | Franke | A61F 5/0111 602/16 |

OTHER PUBLICATIONS

Ankle injury mechanisms: lessons learned from cadaveric studies, Clinical Anatomy 24(3)350-361 (2011).
ASTM F-2413-2005, "Standard Specification for Performance Requirements for Protective Footwear".
Foot and Ankle Trauma collected in the Foot and Ankle (2004) Lippincott.
Labor Occupational Safety and Health Administration regulation part 1910.136 "Foot Protection, and Standard Test Methods for Foot Protection".
Rehabilitation for the Postsurgical Orthopedic Patient (2013) Mosby.

* cited by examiner

*Primary Examiner* — Ophelia A Hawthorne
(74) *Attorney, Agent, or Firm* — Advent, LLP

(57) ABSTRACT

According to various embodiments of this disclosure, an orthopedic rehabilitation device includes a splint, a sole coupled with the splint, and a protective covering. The splint is configured to engage a lower portion of an individual's leg that extends above the individual's ankle. The splint includes at least a first rigid support member that prevents flexing of the lower portion and at least partially immobilizes the individual's ankle. The sole is configured to receive the individual's foot. The sole includes at least a second rigid support member that prevents flexing of the individual's foot. The protective covering is configured to receive the individual's forefoot. The protective covering includes a rigid mesh or solid layer that protects the individual's forefoot from an external force, such as a falling object or any other impact encountered in a work, athletic, training, combat, or other environment where protective apparel is required or recommended.

6 Claims, 11 Drawing Sheets

ENHANCED FOREFOOT PROTECTION FOR ORTHOPEDIC REHABILITATION DEVICES

PRIORITY

The present application claims priority under 35 U.S.C. §119(e) to U.S. Provisional Patent Application Ser. No. 61/885,708, titled ORTHOPEDIC DEVICE FOR LOWER LEG IMMOBILIZATION AND PROTECTION, By David C. Buck, filed Oct. 2, 2013, or is an application of which currently co-pending application(s) are entitled to the benefit of the filing date. The above-referenced provisional patent application is hereby incorporated by reference in its entirety.

FIELD OF INVENTION

The present disclosure generally relates to orthopedic rehabilitation devices for lower extremities and, more specifically, to a lower leg rehabilitation device for treating or mitigating an injury of an individual's foot, ankle, and/or an injury in proximity of an individual's foot and/or ankle.

BACKGROUND

An individual's lower leg (e.g. foot and/or ankle) is prone to a variety of dysfunctions. For example, toes may break or joints may fail from wear or disease. A low leg injury may require surgical intervention to correct soft tissues. There are a variety of means by which ankles are injured and remedied and/or rehabilitated. For example, see *Ankle injury mechanisms: lessons learned from cadaveric studies*, Clinical Anatomy 24(3)350-361 (2011); *Foot and Ankle Trauma collected in The Foot and Ankle* (2004) Lippincott, all incorporated herein by reference. In most cases, rehabilitating an ankle or foot requires immobilization because broken bones must be held in place to properly heal. Surgery also requires a recovery period, sometimes of a long duration, where the patient's use of the foot and/or ankle needs to be restricted. For example, see *Rehabilitation for the Postsurgical Orthopedic Patient* (2013) Mosby, incorporated herein by reference.

Immobilization of the foot, ankle, or both is very inconvenient for a patient. As such, devices that can immobilize the joint while maintaining a patient's mobility are ideal. A variety of orthopedic devices, generally referred to as walking boots, are popular in that they sufficiently immobilize the foot and/or ankle for recovery but maintain patient mobility. For example, a controlled ankle motion ("CAM") walking boot is often provided for patients as a lightweight alternative to a cast. In general, CAM boots are less disruptive to mobility and hygiene (as they can be taken off), and they accomplish the primary objective of immobilizing the foot and ankle to allow proper healing and prevent further injury. However because of their lighter weight design and focus on patient comfort, CAM boots fail to offer patients adequate protection from external forces, such as falling objections that may be encountered in various work or athletic environments (e.g., construction sites, warehouses, gyms, and so forth).

SUMMARY

According to various embodiments of this disclosure, an orthopedic rehabilitation device includes a splint, a sole coupled with the splint, and a protective covering. The splint is configured to engage a lower portion of an individual's leg that extends above the individual's ankle. The splint includes at least a first rigid support member that prevents flexing of the lower portion and at least partially immobilizes the individual's ankle. In implementations, the first rigid support member is included in a side member. In some embodiments, at least two rigid support members are included in side members of the splint (e.g., one on each side of the leg). The sole is configured to receive the individual's foot. The sole includes at least a second rigid support member that prevents flexing of the individual's foot. For example, the sole may include a rigid support member configured to support a majority of the bottom (i.e., the sole) of the individual's foot. The protective covering is configured to receive the individual's forefoot. For example, the protective covering may arc over the individual's toes and/or metatarsal region of the individual's foot. The protective covering includes a rigid mesh or solid layer that protects the individual's forefoot from an external force, such as a falling object or any other impact encountered in a work, athletic training, combat, or other environment where protective apparel is required or recommended.

In some embodiments, the protective covering is detachable from the orthopedic rehabilitation device. The detachable protective covering includes a rigid mesh or solid layer configured to protect an individual's forefoot from an external force. The rigid mesh or solid layer may include a plurality of connectors configured to receive straps that compress the sole and/or splint of the orthopedic device with the individual's foot and/or a lower portion of the individual's leg. The connectors enable the rigid mesh or solid layer to be fastened to the orthopedic device. For example, the detachable protective covering can be placed over the individual's forefoot, substantially covering the individual's toes, and can be firmly held in place with the straps extending from the splint and/or sole of the orthopedic rehabilitation device.

In some embodiments, the splint includes a front member and a rear member configured to engage a lower portion of an individual's leg that extends above the individual's ankle. The first rigid support member (or multiple splint support members) may be integrated or coupled with the front member or the rear member. For example, the splint support members may be integrated in side members that can be coupled (e.g., via straps) to the front and/or rear member. To facilitate placement of the individual's foot and lower leg within the orthopedic device without substantial being of the individual's ankle and/or flexing of the individual's foot, the rear member may be configured to detach or partially disengage from the front member or side members. For example, the rear member may be at least partially removed or bent back via one or more hinges positioned along the back of the orthopedic rehabilitation device.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The various embodiments of the disclosure may be better understood by those skilled in the art by reference to the accompanying figures, briefly summarized below.

DETAILED DESCRIPTION

Reference will now be made in detail to the subject matter disclosed, which is illustrated in the accompanying drawings.

Figure 1:
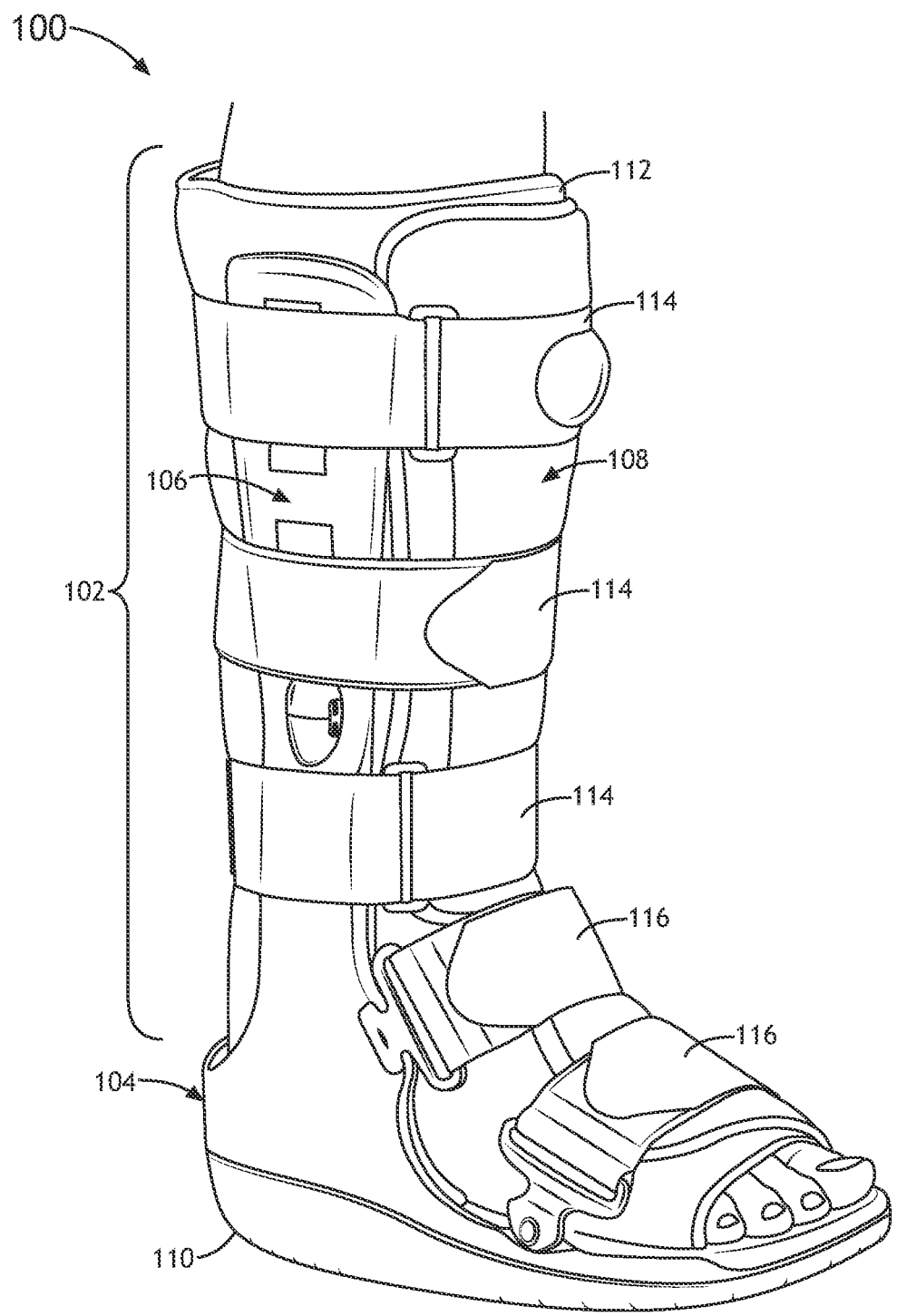
FIG. 1 depicts an orthopedic rehabilitation device, in accordance with an embodiment of this disclosure.

FIGS. 1 through 11 illustrate an orthopedic rehabilitation device 100 in accordance with various embodiments of this disclosure. As shown in FIG. 1, the orthopedic rehabilitation device 100 may include a controlled ankle motion ("CAM") walking boot. The term "CAM walking boot" describes a variety of orthopedic devices that include a splint 102 attached to a sole 104. Orthopedic devices having the foregoing structural elements are sometimes referred to by alternative names, including but not limited to: a CAM boot, a CAM walking boot, a fracture boot, a walking boot, a cast boot, a walking cast boot, a walking splint, a walking brace, a medical walking boot, or a controlled range of motion ("CROM") walker.

Figure 2:
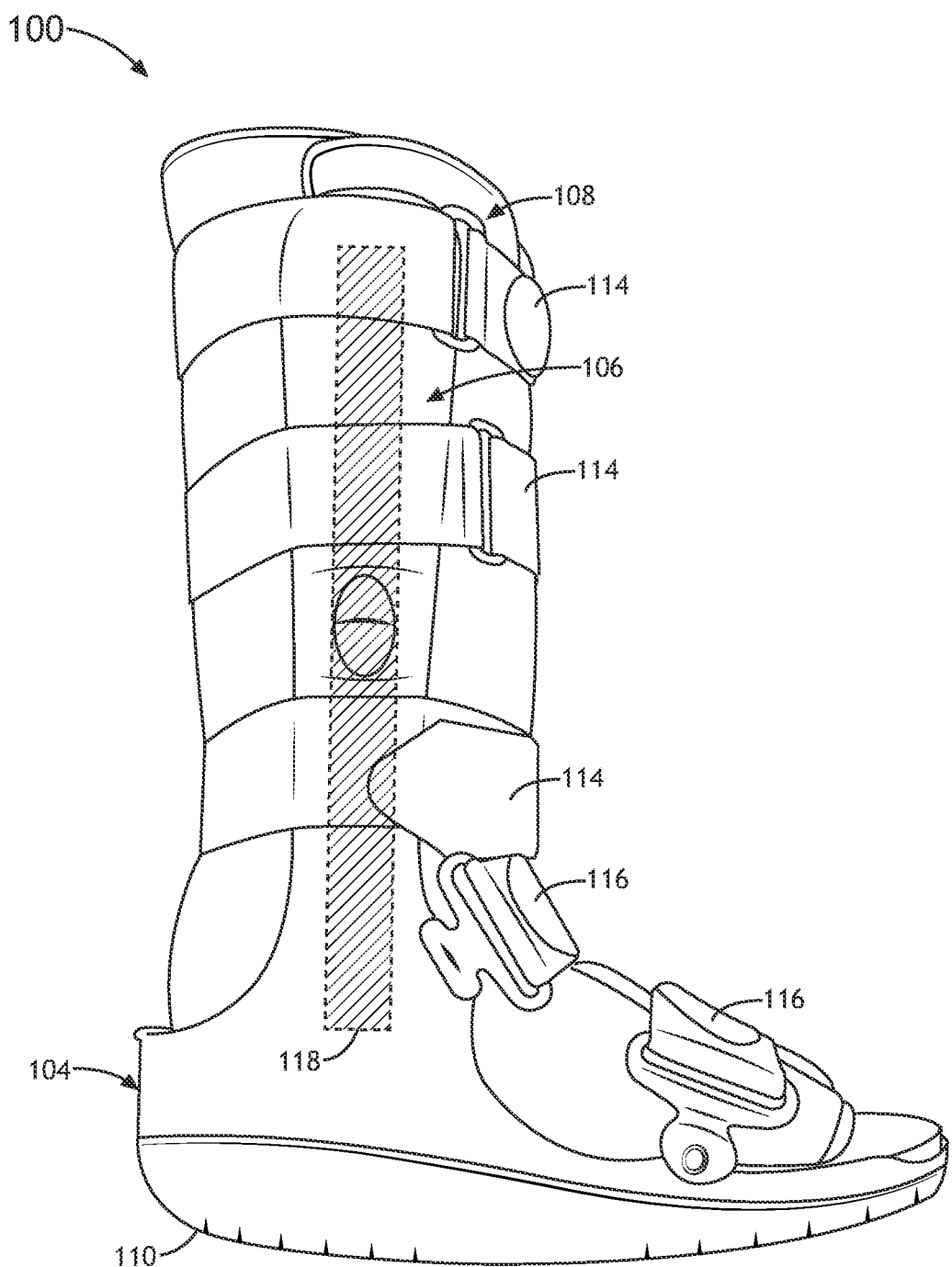
FIG. 2 depicts an orthopedic rehabilitation device including at least one rigid support member that extends along a lower portion of an individual's leg, in accordance with an embodiment of this disclosure.

In some embodiments, the splint 102 includes side members 106 configured to receive a lower portion of an individual's leg. For example, each side member 106 may be configured to engage a portion of the individual's leg extending above the ankle. As shown in FIG. 2, at least one of the side members 106 includes a rigid support member 118 (sometimes referred to herein as a "splint support member 118") that stabilizes or prevents flexing of the lower portion of the individual's leg and at least partially works to immobilize the individual's ankle when the orthopedic rehabilitation device 100 is tightly fastened. In some embodiments, each of the side members 106 includes a respective splint support member 118. Alternatively or additionally, the one or more splint support members 118 may be included in a front or rear member of the splint 102. The splint 102 may further include a front member 108 located between the side members 106. The front member 108 may be configured to cover a front side of the lower portion of the individual's leg (e.g., a lower portion of the shin). In some embodiments, the front member 108 is integrated with (i.e., includes) the side members 106 or may be permanently/removably coupled with the side members 106.

Figure 3:
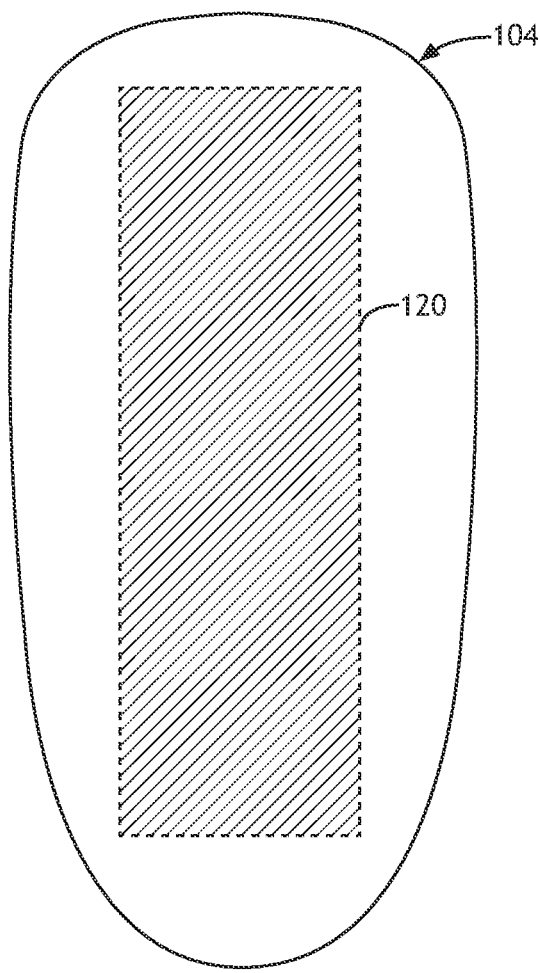
FIG. 3 depicts a sole of an orthopedic rehabilitation device including at least one rigid support member that underlies a bottom portion of an individual's foot, in accordance with an embodiment of this disclosure.

As shown in FIG. 3, at least a second support member 120 (sometimes referred to herein as a "sole support member 120") is included in the sole 104. The sole support member 120 is configured to stabilize and/or prevent flexing of the individual's foot. The sole 104 may include a curved bottom surface 110 so that the individual can 'rock' her foot, thus minimizing the need to move her ankle. Where the sole 104 includes a curved bottom surface 110, the curvature may be such that the widest part of the sole 104 is underneath the center or just off the center of the individual's foot. As a result, the walking motion of the individual tends to rock the sole 104 in the direction of ordinary footfall. This facilitates normal walking prevents substantial interruption of gait due to the immobilized ankle. Further, the sole support member 120 prevents bending of the individual's foot.

In some embodiments, for comfort and safety of the patient, the splint 102 may be at least partially covered (internally) by a sock 112, such as a soft sleeve made of microfiber cloth and/or padding that functions as a barrier between the splint 102 and the individual's lower leg. The sock 112 may be designed to cover all or substantially all of the individual's lower leg, which may or may not include the individual's foot.

The orthopedic rehabilitation device 100 further includes a plurality of straps 114/116 that tightly fasten the splint 102 and the sole 104 to the individual's lower leg and foot. When the straps 114/116 are tightened, the splint 102 and sole 104 are compressed with the individual's lower leg and foot, and as a result, the rigid support members 118 and 120 are enabled to immobilize individual's the foot and ankle. In some embodiments, the splint 102 is tightly fastened by one or more straps 114 located above the ankle, and the sole is tightly fastened by one or more straps 116 located at or below the ankle. In some embodiments, at least one strap 116 is aligned with the ankle and configured to firmly hold the individual's heel in contact with the back of the sole 104.

In some embodiments, the upper straps 114 wrap around the circumference of the splint 114. The straps 114 adjust to accommodate a wide variety of leg and foot sizes. The straps 114 may be held together and/or tightened with any fastener or fastening configuration known to the art. For example, the straps 114 may fasten by hook and loop configurations, VELCRO connectors, buttons, buckles, ties, or the like. The fasteners hold the straps tightly around the splint and can further operate to adjust the size (e.g., circumference) of the splint 114. The lower straps 116 (if any) can be similarly structured to accommodate various foot sizes (e.g., widths and/or heights). Importantly, the straps 114/116 compress the underlying components of the orthopedic device 100, snugly holding individual's lower leg, ankle, and foot in contact with the splint 102 and sole 104 to effectively immobilize the individual's ankle and prevent flexing of her foot.

The straps 114/116 may be adjustable to fit a wide variety of individuals, and to avoid exacerbating an injury, the straps 114/116, when loosened or unfastened, may allow sufficient movement of components making up the splint 102 and/or sole 104 to receive the individual's lower leg without substantial bending of her foot or ankle. When tightened, the straps 114/116 compress the one or more splint support members 118 to the individual's lower leg, which in turn immobilizes the individual's ankle.

In order to be effective, the one or more splint support members 118 and the sole support member 120 are formed from a substantially rigid structure. In various embodiments, each splint support member 118 and/or sole support member 120 incorporates a plate or rod made of a steel alloy or other rigid (but light weight) metal or metal alloy. Alternatively, the splint support member 118 and/or the sole support member 120 may be formed from a rigid composite material such as durable plastic or carbon fiber. In some embodiments, the splint 102 and the sole 104 may be formed together out of one body. For example, a high density plastic, carbon fiber, or other composite shell may provide sufficient rigidity for the splint 102 and the sole 104. In such embodiments, the splint 102 and the sole 104 effectively function as the rigid support members 118 and 120 and are said to be "integrated with" the rigid support members 118 and 120.

Figure 4:
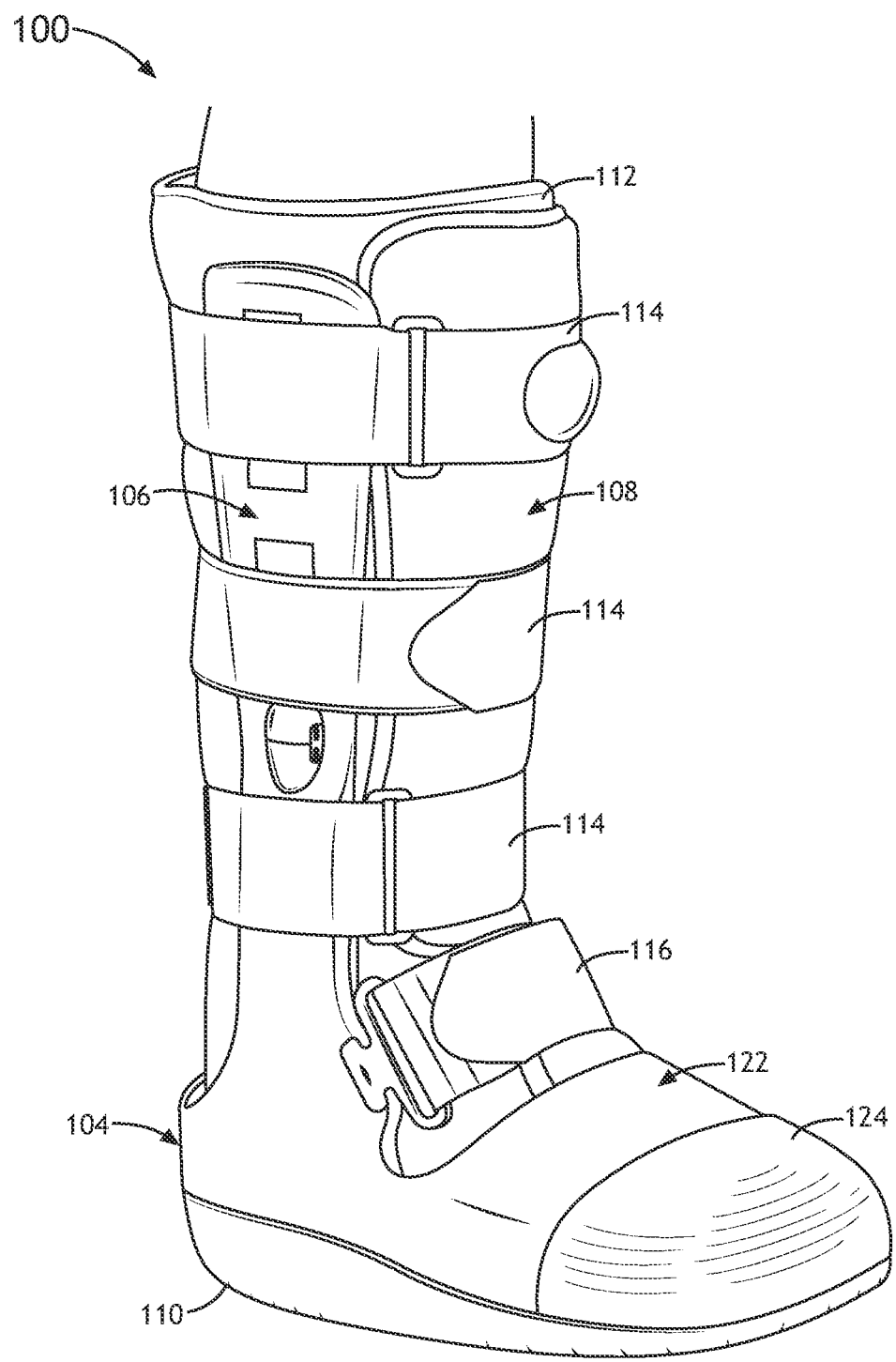
FIG. 4 depicts an orthopedic rehabilitation device including a protective covering that arcs over an individual's toes, in accordance with an embodiment of this disclosure.

FIG. 4 shows an embodiment of the orthopedic rehabilitation device 100 including a protective forefoot covering 122 including a reinforced toe covering 124. Protective forefoot coverings are discussed in several publications, such as U.S. Pat. Nos. 6,604,303, 2,354,338, 2,756,519, 3,444,572, and 3,798,804, which are all incorporated herein by reference. The inclusion of a protective toe covering in CAM walking boots would typically be viewed as diminishing the lightweight design and encumbering the desired ease of access. That is, the individual should be able to wear or remove the orthopedic rehabilitation device 100 with limited ankle movement or bending of the foot. Furthermore, most CAM walking boots are made with economy in mind.

The structure of a typical CAM walking boot is such that the splints are formed to accommodate a wide variety of foot, leg and ankle sizes. The plurality of fasteners operate to conform the device to a wide variety of foot shapes. As a result, the upper surfaces that cover the foreleg, top of the foot, and/or toes are generally formed from soft materials (e.g., padding and/or cloth) and offer limited protection for the foot, especially from heavy or hard objects that may fall upon or otherwise impact any portion (e.g., toes) of the foot. Federal or state regulations may prevent individuals employed in workplaces subject to footwear protection requirements from wearing CAM walking boots to work. For example, see the United States Department of Labor Occupational Safety and Health Administration regulation part 1910.136 "Foot Protection, and Standard Test Methods for Foot Protection," and ASTM F-2413-2005, "Standard Specification for Performance Requirements for Protective Footwear," both incorporated herein by reference. Because of the various practical and/or legal concerns, an individual with a lower leg injury is often unable to perform her employment duties or even enter certain work sites (e.g., construction or manufacturing sites), athletic environments (e.g., gyms or training sites), combat zones, or other environments where protective apparel is required or recommended while the individual is recovering from her injury. In some instances, the individual is prevented from working even if the injury would not interfere with the individual's ability to perform the duties of her job.

Figure 5:
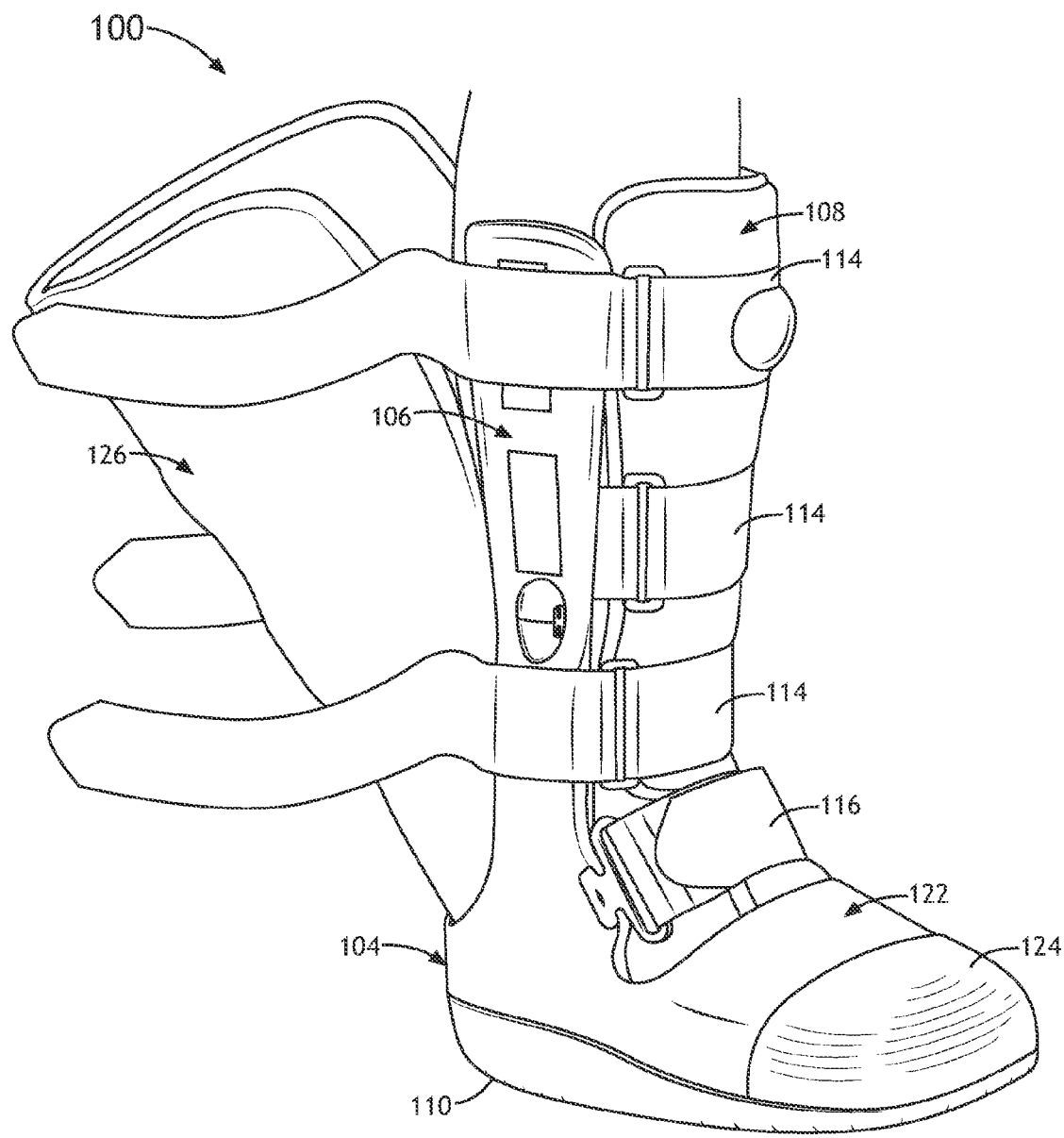
FIG. 5 depicts an orthopedic rehabilitation device including a protective covering that arcs over an individual's toes and further including a rear member that at least partially disengages (i.e., actuates to an open position), in accordance with an embodiment of this disclosure.
Figure 6:
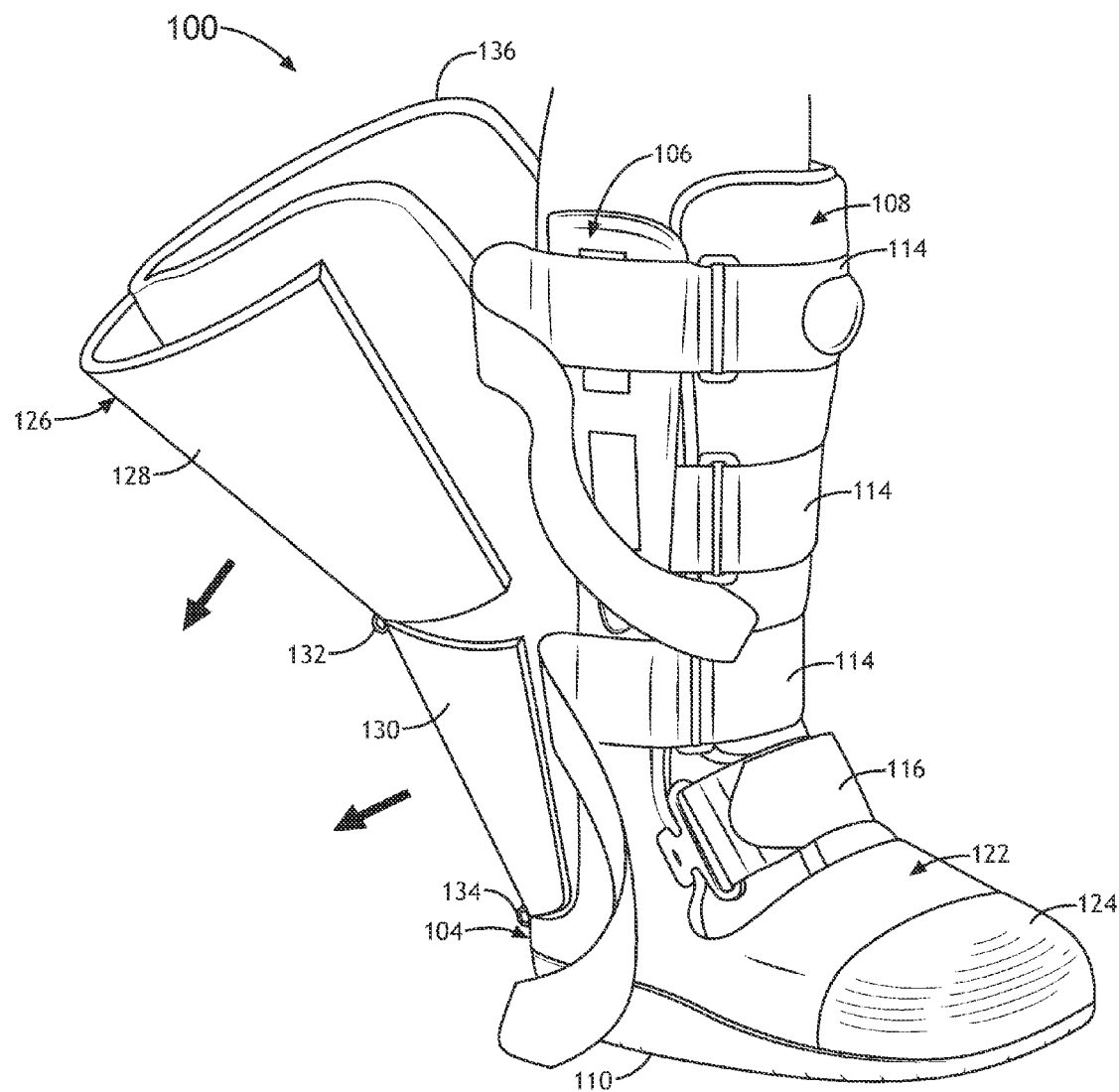
FIG. 6 depicts an orthopedic rehabilitation device including a protective covering that arcs over an individual's toes and further including a rear member that at least partially disengages (i.e., actuates to an open position) via two or more hinges, in accordance with an embodiment of this disclosure.
Figure 7:
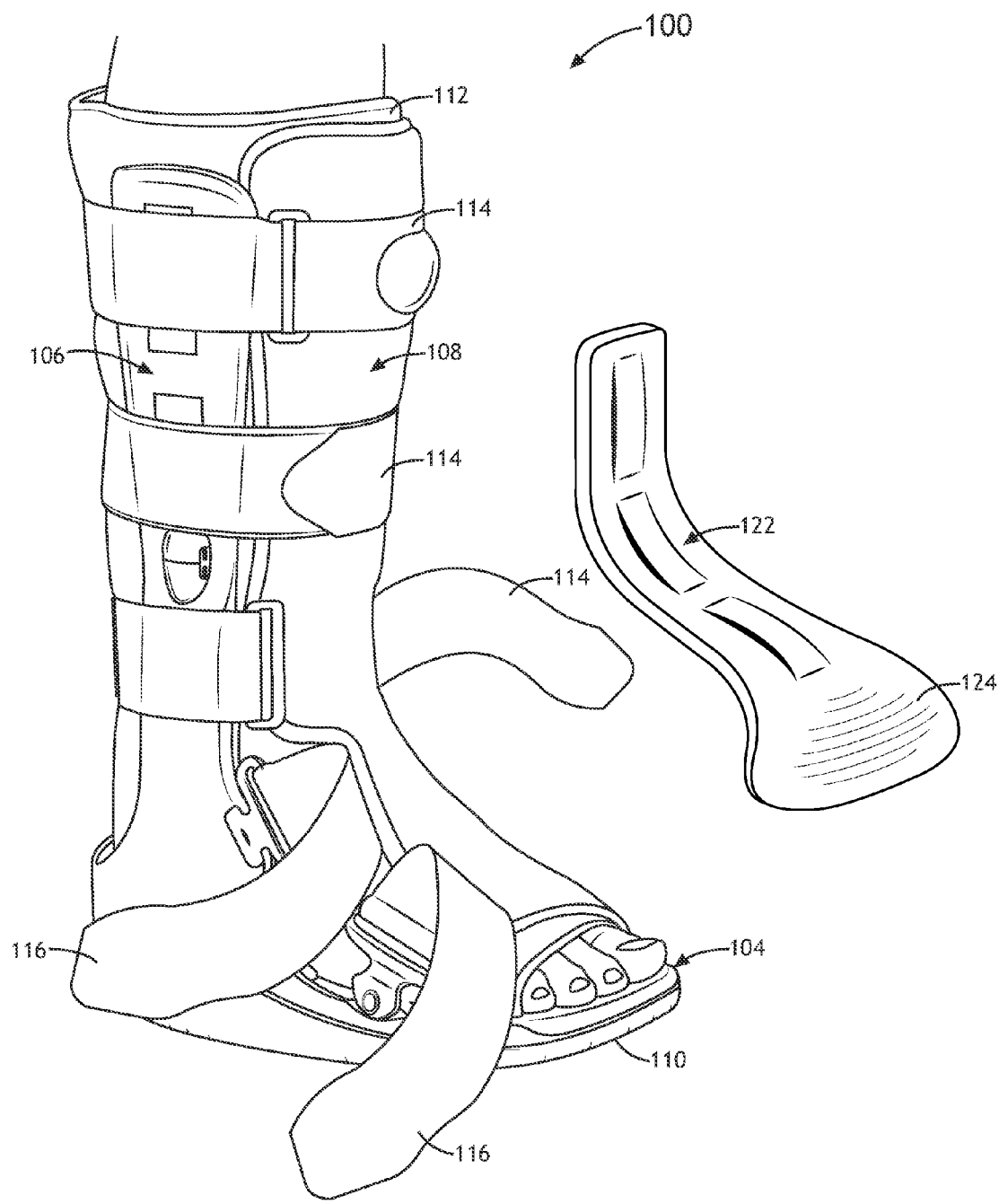
FIG. 7 depicts a detachable protective covering for an orthopedic device, in accordance with an embodiment of this disclosure.
Figure 8:
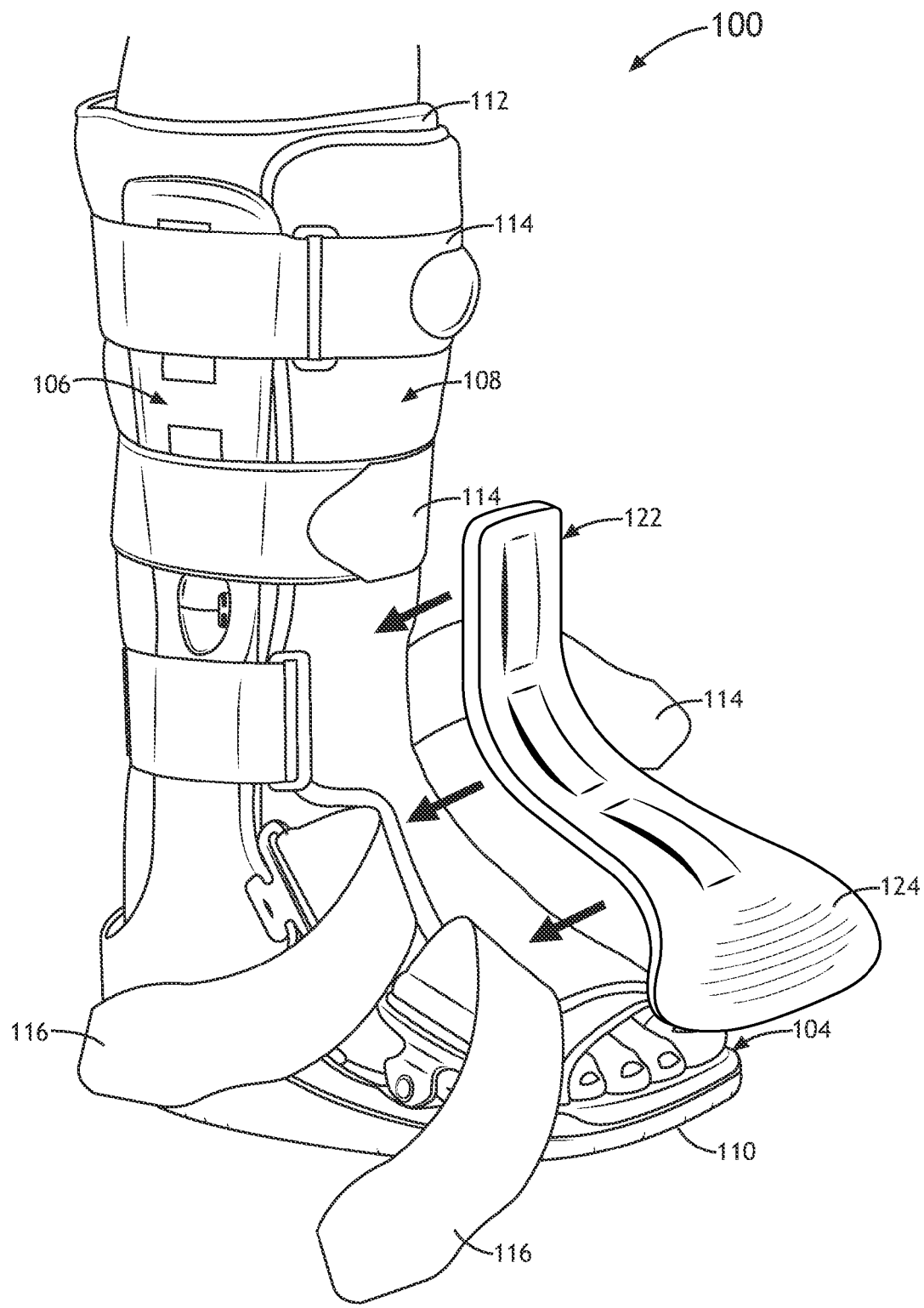
FIG. 8 depicts a detachable protective covering for an orthopedic device, in accordance with an embodiment of this disclosure.
Figure 9:
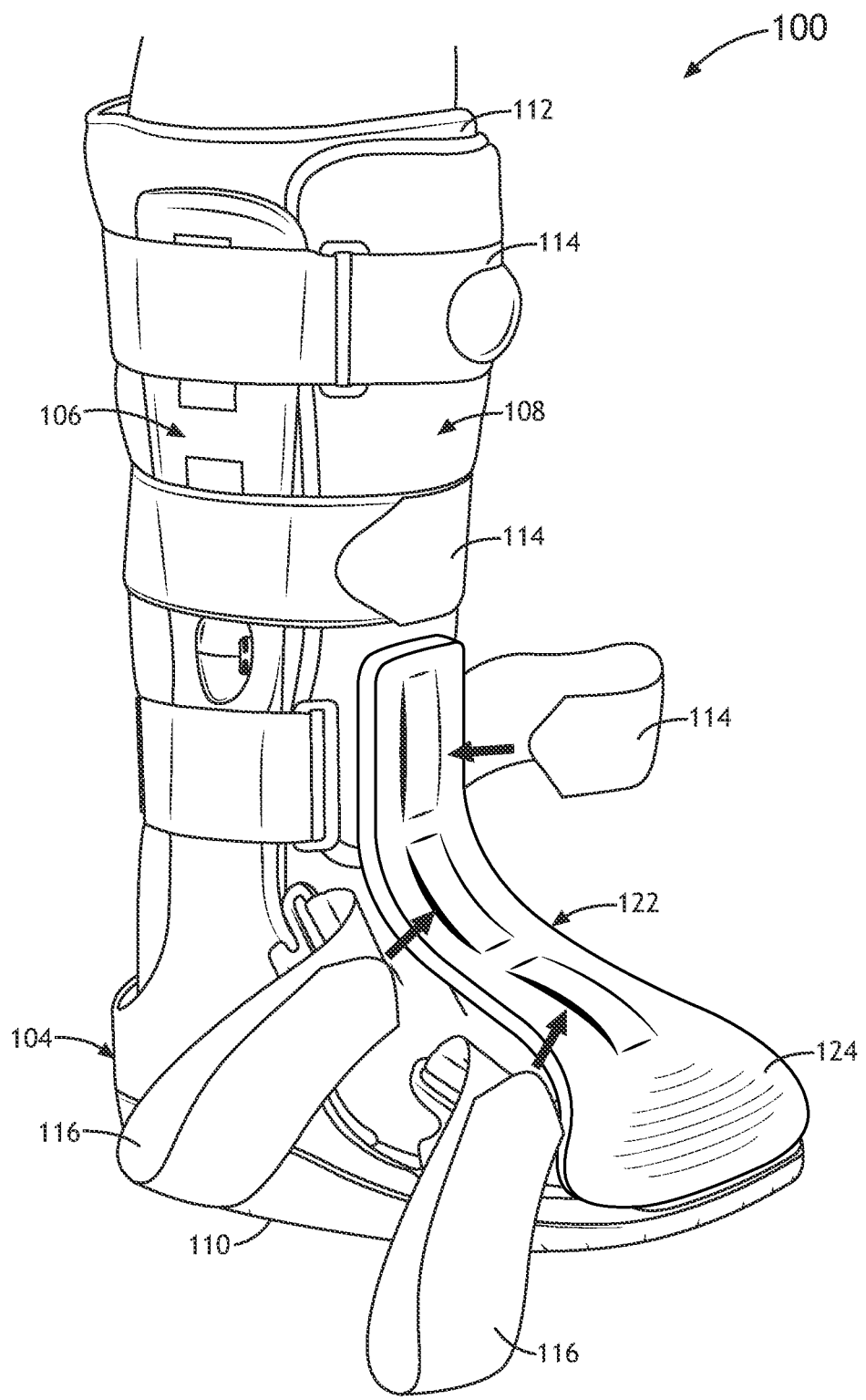
FIG. 9 depicts a detachable protective covering for an orthopedic device, in accordance with an embodiment of this disclosure.
Figure 10:
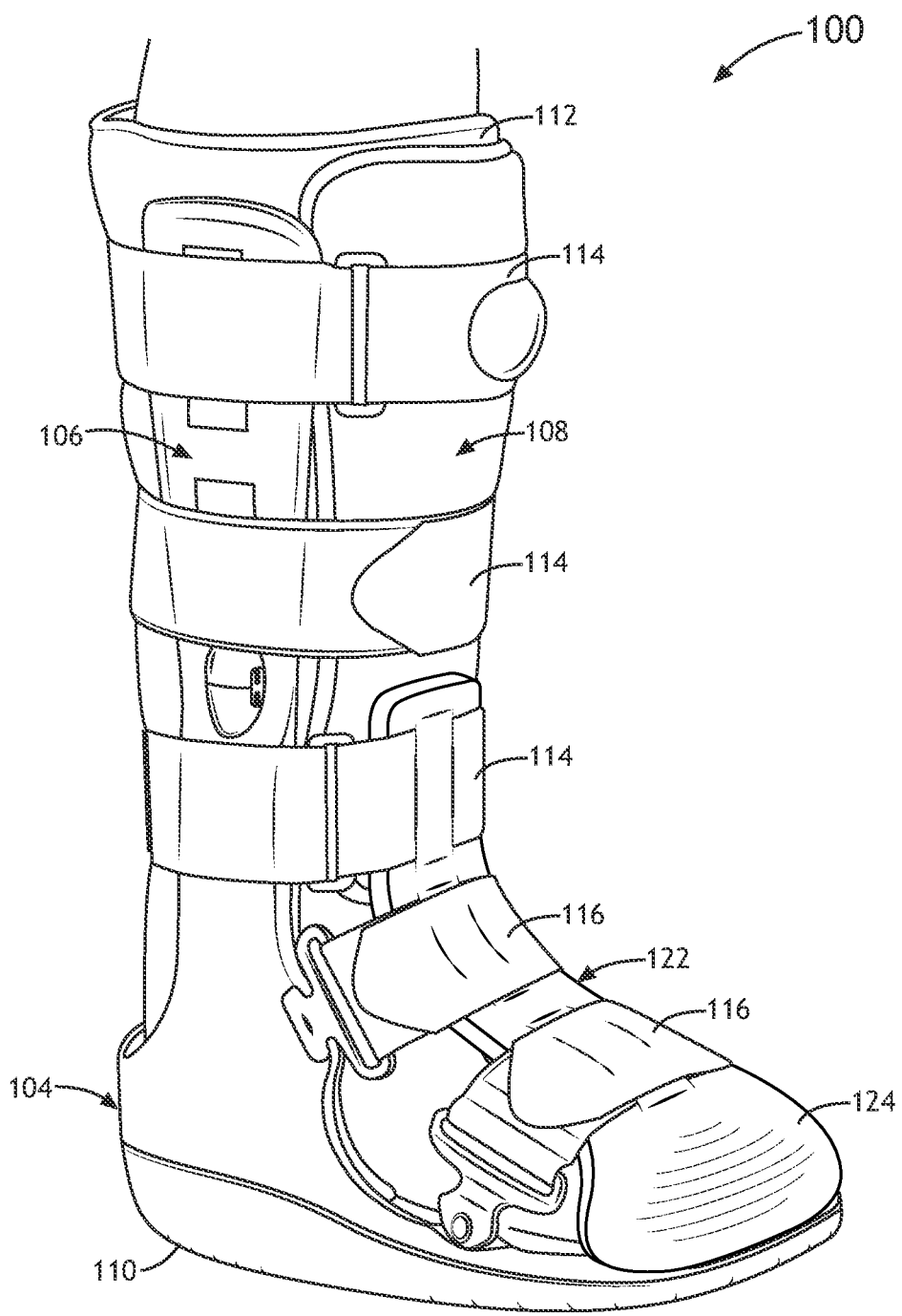
FIG. 10 depicts a detachable protective covering for an orthopedic device, in accordance with an embodiment of this disclosure.

The protective covering 122 can be integrated with the splint 102 and/or sole 104. Alternatively, the protective covering 122 can be detachable (as shown in FIGS. 7 through 11). FIGS. 4 through 6 illustrate embodiments where the protective covering 122 is coupled or integrated with the sole 104, forming a shoe-like structure that receives the individual's foot. The toe covering 124 may be a rigid mesh or solid layer forming at least a portion of the protective covering 122 that arcs over and protects the individual's forefoot from external forces. In some embodiments, the toe covering 124 is a metallic layer (e.g., a mesh cage-like layer or solid plating) including a steal alloy or the like. Alternatively, the toe covering 124 may include a composite layer formed from carbon fiber, fiberglass, durable plastic, a network of plastic members, or the like. To sufficiently protect the individual's forefoot from falling objects or other impacts, the toe covering 124 may be configured to withstand an impact of at least 75 foot-pounds. In some embodiments, the protective covering 122 (inclusive or exclusive of the toe covering 124) is also formed from a durable (e.g., rigid or semi-rigid) material such as a composite material (e.g., carbon fiber, fiberglass, durable plastic, or the like). The protective covering 122, as a whole, may be configured to arc over and protect at least the front third of the individual's foot.

As discussed above, it is important to enable the individual to insert her lower leg into the splint without substantial bending of the ankle or flexing of the foot in order to avoid exacerbating her injury. This can be accomplished a number of ways. In implementations, the splint 102, sole 104, and/or protective covering 122 may be detachable from at least one of the other components or configured to partially disengage (i.e., transition to an open position) to facilitate easy access for the individual. For instance, the front member 108, the side members 106, and/or a rear member 126 forming the splint 102 may be configured to detach or at least partially disengage from the other components to enable comfortable insertion of the individual's lower leg. Alternatively, the protective covering 122 may be configured to detach or partially disengage from the splint 102 and/or sole 104. In some embodiments, a combination of elements may be detachable and/or configured to actuate relative to one another to provide easy access for the individual.

As shown in FIGS. 5 and 6, the orthopedic rehabilitation device 100 may include an actuatable or detachable rear member 126 that is at least partially removed or transitioned to an open position allowing the individual to comfortable insert her lower leg into the splint 102 without substantial movement of her ankle or stress on her foot. To enable the rear member 126 to open/close the straps 114 may be extend from the front of the splint 102 to the rear. In some embodiments, the rear member 126 bends back at least 45 degrees from a hinge located at or just above the back of the sole 104. The rear member 126 may be formed from a padding or other semi-rigid material for a comfortable and lightweight design. Alternatively, the rear member 126 may be formed from a composite material or plastic for added support. To facilitate entry of the individual's lower leg, especially where the rear member 126 is formed from a rigid material, the rear member 126 may be divided into at least two sections (e.g., an upper section 128 and a lower section 130) that transition from a closed position to an open position as shown in FIG. 6. In some embodiments, the upper section 128 is configured to actuate at least 45 degrees from a first hinge 132 located between the upper section 128 and the lower section 130, and the lower section 132 is configured to actuate at least 15 degrees from a second hinge 130 located at or just above the back of the sole 104. In some embodiments, the rear member 126 is formed from a substantially rigid material; however for comfort and safety of the individual, the orthopedic device 100 may include a padding 136 under the rear member 126 or lining (i.e., coupled to an inner surface of) the rear member 126.

Figure 11:
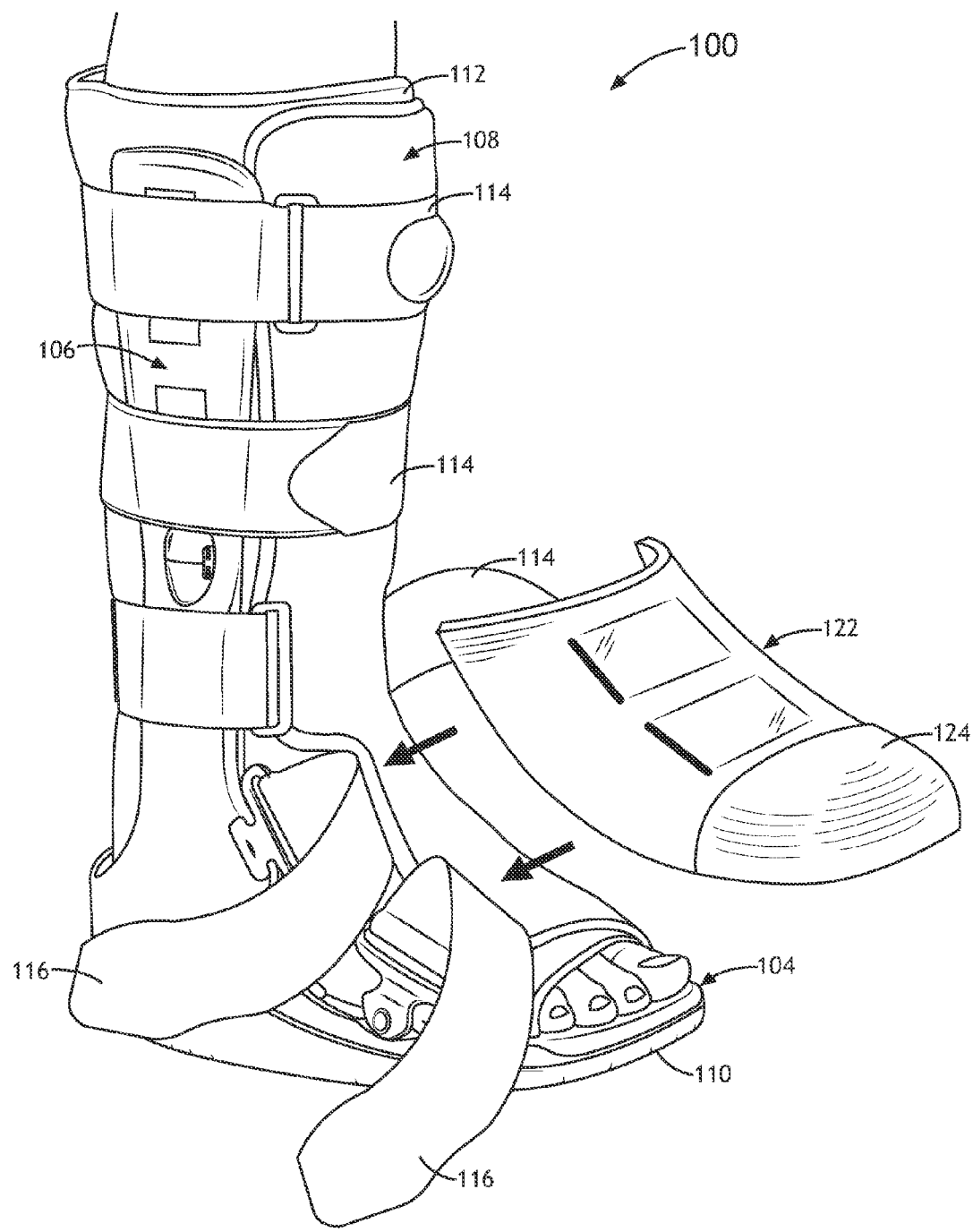
FIG. 11 depicts a detachable protective covering for an orthopedic device, where the detachable protective covering extends over the sides and toes of an individual's foot, in accordance with an embodiment of this disclosure.

FIGS. 7 through 11 illustrate embodiments where the protective covering 122 is detachable or configured to at least partially disengage from the splint 102 and/or sole 104. For example, the protective covering 122 may be a distinct structural element that is connected to the orthopedic rehabilitation device 100 after both are independently manufactured. Alternatively, the protective covering 122 may be manufactured with the orthopedic rehabilitation device 100 but, nevertheless, configured to detach or partially disengage from the splint 102 and/or sole 104 (e.g., via one or more hinges) to allow the individual to wear the orthopedic rehabilitation device 100 as she would wear a typical CAM boot. That is, the individual may be enabled to unfasten the straps 114/116 to open the front of the splint 102, insert her leg, place the protective covering 122 over her forefoot, and lock it into place with cooperative fasteners and/or by placing the straps 114/116 through a plurality of connectors (e.g., loops, slits, grooves, or the like). FIGS. 7 through 10 illustrate a method by which the straps 114/116 are used to couple a detachable protective covering 122 to the orthopedic rehabilitation device 100. FIG. 11 illustrates an embodiment where the detachable protective covering 122 is larger and configured to arc over and protect at least the front third of the individual's foot (i.e., covering sides of the forefoot in addition to the toes).

It is further contemplated, that a mixture of elements from the foregoing embodiments could be employed to achieve ease of access, comfort, and/or manufacturability advantages. It will be understood by those within the art that, in general, terms used herein, and are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

What is claimed is:

1. An orthopedic rehabilitation device, comprising:
   a splint including a front member, two side members, and a rear member configured to engage a lower portion of an individual's leg that extends above the individual's ankle, the splint further including at least a first rigid support member that prevents flexing of the lower portion and at least partially immobilizes the individual's ankle, the first rigid support member being included in at least one of the two side members, the rear member being configured to detach or partially disengage from the two side members to enable placement of the lower portion of the individual's leg within the splint without substantial bending of the individual's ankle or flexing of the individual's foot;
   a sole configured to receive the individual's foot, the sole including at least a second rigid support member that prevents flexing of the individual's foot;
   a plurality of straps configured to compress the splint and the sole with the lower portion of the individual's leg and the individual's foot, respectively; and
   a protective covering configured to receive the individual's forefoot, the protective covering including a rigid mesh or solid layer that protects the individual's forefoot from an external force.

2. The orthopedic rehabilitation device of claim 1, wherein the rear member hinges from the sole and is configured to actuate 45 degrees from a closed position in contact or near proximity of the two side members to an open position for placement of the lower portion of the individual's leg within the splint.

3. The orthopedic rehabilitation device of claim 1, wherein the rear member comprises a lower section hinging from the sole and an upper section hinging from the lower section, the lower section and the upper section being configured to actuate 15 degrees and 45 degrees, respectively, from closed positions to open positions for placement of the lower portion of the individual's leg within the splint.

4. The orthopedic rehabilitation device of claim 1, wherein the rigid mesh or solid layer of the protective covering comprises a metal layer including a steel alloy.

5. The orthopedic rehabilitation device of claim 1, wherein the rigid mesh or solid layer of the protective covering comprises a composite layer including at least one of carbon fiber, fiberglass, or durable plastic.

6. The orthopedic rehabilitation device of claim 1, wherein the rigid mesh or solid layer of the protective covering is configured to withstand an impact of 75 foot-pounds from the external force.

\* \* \* \* \*